(12) United States Patent
D'Atri et al.

(10) Patent No.: US 8,093,218 B2
(45) Date of Patent: Jan. 10, 2012

(54) PEPTIDE DERIVED FROM VASCULAR ENDOTHELIAL GROWTH FACTOR RECEPTOR-1 BINDING INTEGRIN α5β1 HAVING PROANGIOGENIC ACTIVITY

(75) Inventors: Stefania D'Atri, Rome (IT); Cristina Maria Failla, Rome (IT); Pedro Miguel Lacal, Rome (IT); Angela Orecchia, Rome (IT); Giovanna Zambruno, Rome (IT); Anna Tramontano, Rome (IT); Simonetta Soro, Rome (IT); Veronica Morea, Rome (IT)

(73) Assignees: Provincia Italiana della Congregazione dei Figli dell'Immacolata Concezione-Istituto Dermopatico dell'Immacolata, Rome (IT); Consiglio Nazionale delle Richerche, Rome (IT); Universita' degli Studi di Roma "La Sapienza", Rome (IT)

( * ) Notice: Subject to any disclaimer, the term of this patent is extended or adjusted under 35 U.S.C. 154(b) by 113 days.

(21) Appl. No.: 12/375,775

(22) PCT Filed: Jul. 31, 2007

(86) PCT No.: PCT/IT2007/000551
§ 371 (c)(1),
(2), (4) Date: May 11, 2009

(87) PCT Pub. No.: WO2008/015720
PCT Pub. Date: Feb. 7, 2008

(65) Prior Publication Data
US 2009/0312266 A1    Dec. 17, 2009

(30) Foreign Application Priority Data

Jul. 31, 2006  (IT) ................. RM2006A000409

(51) Int. Cl.
*A61K 38/08* (2006.01)
*C07K 7/06* (2006.01)
(52) U.S. Cl. ...................................... 514/21.8; 530/330
(58) Field of Classification Search ........................ None
See application file for complete search history.

(56) References Cited

U.S. PATENT DOCUMENTS
5,661,127 A *  8/1997  Bhatnagar et al. ............ 424/484

FOREIGN PATENT DOCUMENTS
WO    2005/036177    4/2005

OTHER PUBLICATIONS

International Search Report dated Feb. 22, 2008, from corresponding PCT application.
Angela Orecchia et al., "Vascular endothelial growth factor receptor-1 is deposited in the extracellular matrix by endothelial cells and is a ligand for the alpha5bebeta integrin", Journal of cell science, vol. 116, No. 17, Sep. 1, 2003, XP002468572, 3479-3489.
A. Orecchia et al., "Soluble vascular endothelial growth factor-1 could represent a positive mediator in the angiogenic process", XP002468573, Databse Biosis [Online], XP002468573.
Database accession No. PREV200700144740, & Journal of Investigative Dermatology, vol. 126, No. Suppl. 3, Aug. 2006, p. 10, XP002468574, 36th Annual Meeting of the European-Society-Of-Dermatology-Research (ESDR); Sep. 6-7, 2006.

* cited by examiner

*Primary Examiner* — Prema Mertz
(74) *Attorney, Agent, or Firm* — Young & Thompson

(57) ABSTRACT

Description of a sequence peptide isolated in the domain II type-immunoglobulin (Type-Ig) of the Vascular Endothelial Growth Factor receptor 1 (VEGF-1) binding integrin α5β1, usable for the preparation of pharmacological agents having proangiogenic activity.

4 Claims, 7 Drawing Sheets

A

B

PEPTIDE DERIVED FROM VASCULAR ENDOTHELIAL GROWTH FACTOR RECEPTOR-1 BINDING INTEGRIN α5β1 HAVING PROANGIOGENIC ACTIVITY

The present invention refers to the field of molecular Biology and in particular to one peptide sequence isolated in domain II type-Ig of the VEGFR-1 able to bind and to activate the integrin α5β1. In particular, the isolated sequence peptide, object of the present invention, can favourably be employed for the preparation of pharmacologic agents having proangiogenic activities in the treatment of pathologies that benefit from the formation of new blood vessels.

Vascular endothelial growth factor receptor-1 (VEGFR-1) is a tyrosine kinase receptor for specific members of the vascular endothelial growth factor (VEGF) family. VEGFR-1 is closely related to the type III tyrosine kinase-Fms/Kit/platelet derived growth factor receptors, but it is classified, with VEGFR-2 and VEGFR-3, into a distinct class of receptors whose extracellular region is composed of seven immunoglobulin (Ig)-like domains. Ig-like domain II comprises the region involved in VEGF and placenta growth factor (PlGF) binding, whereas Ig-like domains III and IV are involved in heparin binding, and domain III is also responsible for interaction with neuropilin-1.

The VEGFR-1 is expressed mainly from the endothelial and smooth muscular cells, but also from other cellular types of the haematopoietic lineage and from the cells of the skeletal muscle. The signal transduction in the cell from the VEGFR-1, as a result of the interaction with the growth factor, is not well known.

Gene knockout studies demonstrated that VEGFR-1 is essential for the development and differentiation of embryonic vasculature, and that its inactivation results in increased hemangioblast commitment and disorganization of blood vessels. However, mice carrying a homozygous deletion of the intracellular kinase domain show a correct blood vessel development, this result suggests that the extracellular region of VEGFR-1 is sufficient to support embryonic angiogenesis.

The tyrosine kinase activity of the VEGFR-1 is essential for the chemotactic signaling induced from VEGF and PlGF in monocyte-macrophage and in the haematopoietic stem cells.

Studies on the PlGF, a specific ligand of the VEGFR-1, have demonstrated that this receptor is been involved in the pathological angiogenesis in adults.

More recently it has been demonstrated that growth factors that bind the VEGFR-1 can induce the trans-phosphorylation of VEGFR-2 and that the stimulation of the angiogenesis can be obtained by the formation of heterodimeric complex VEGFR-1/VEGFR-2.

In addition to the transmembrane isoform of VEGFR-1, endothelial cells (EC) produce a soluble form of the receptor, arising from alternative splicing of the same gene. Soluble VEGFR-1 (sVEGFR-1) comprises the first six Ig-like domains of the extracellular region of the receptor and a specific 30 amino acid tail at its C-terminus. Both isoforms bind VEGF with high affinity, and sVEGFR-1 acts as a potent antagonist of VEGF signaling by sequestering the growth factor and thereby inhibiting its interaction with the transmembrane receptors.

The inventors previously demonstrated that sVEGFR-1 secreted by EC in culture becomes part of the extracellular matrix and is able to mediate EC adhesion through direct binding to α5β1 integrin.

A key role of this integrin in promoting vasculogenesis and angiogenesis has been previously highlighted by the defective vascular phenotype of α5 knockout mice and by the ability of either antibodies raised against this integrin or antagonist peptides to block in vitro and in vivo angiogenesis.

Integrin binding to their ligands usually occurs through recognition of short amino acid sequences. Many integrins, including α5β1, bind to arginine-glycine-aspartic acid (RGD) containing peptides, although other motifs have also been identified.

On the basis of what was known to the state of technical, and on the assumption that the sequence of sVEGFR-1 does not contains RGD motif, the inventors of this invention focused their intention on identification of the molecular determinants responsible for its interaction with integrin α5β1.

Experiments, below detail described, was first revealed that an antibody against a peptide mapping on the domain II type-ig prevents the binding of VEGF-1 with integrin α5β1. Therefore, the experimental efforts were focused on this domain II that supports both the accession of EC that the direct link with integrin α5β1.

Subsequently, on the basis of the information available in the experimentally determined structures of this domain II, were developed twelve peptides putatively mimicking the whole surface of the domain, which were subsequently tested for the interaction with the integrin. Of these twelve peptides one was able both to support the accession of EC, that to compete with the accession of the EC sVEGFR-1, and the migration of EC to the sVEGFR-1.

Furthermore, the peptide showed proangiogenic activity in vitro. The replacement with alanine scanning mutagenesis of the peptide has, finally, made it possible to identify the residues of the peptide responsible for its biological activity, which represent a binding motif for the integrin α5β1.

Therefore, it is object of the present invention a peptide having sequence NYLTHRQ with same proangiogenic effect as well as the peptide of sequence YLXHR in which X it can be whichever amino acid, but preferably is Thr/T.

Another object of the present invention is the Use of this peptides for the preparation of a pharmacological compound, suitable for the treatment of the clinical conditions that need the induction of the angiogenesis, such as: peripheral hypertension, vascular diabetes-dependent pathologies, wound, ischemia of the muscle, the brain, the kidney, the intestine, the heart or the limbs, serious occlusive or obstructive vascular pathologies, peripheral vascular pathologies, pericardic ischaemia, infarct whichever vascular pathologies.

Another object of the present invention is the use of peptides in order to direct molecules or particles also viral particles towards integrin α5β1.

Further features of the present invention will turn out clearer from the detailed description, equipped from the experiments, that it follows with reference to the attached figures in which.

Figure 1:
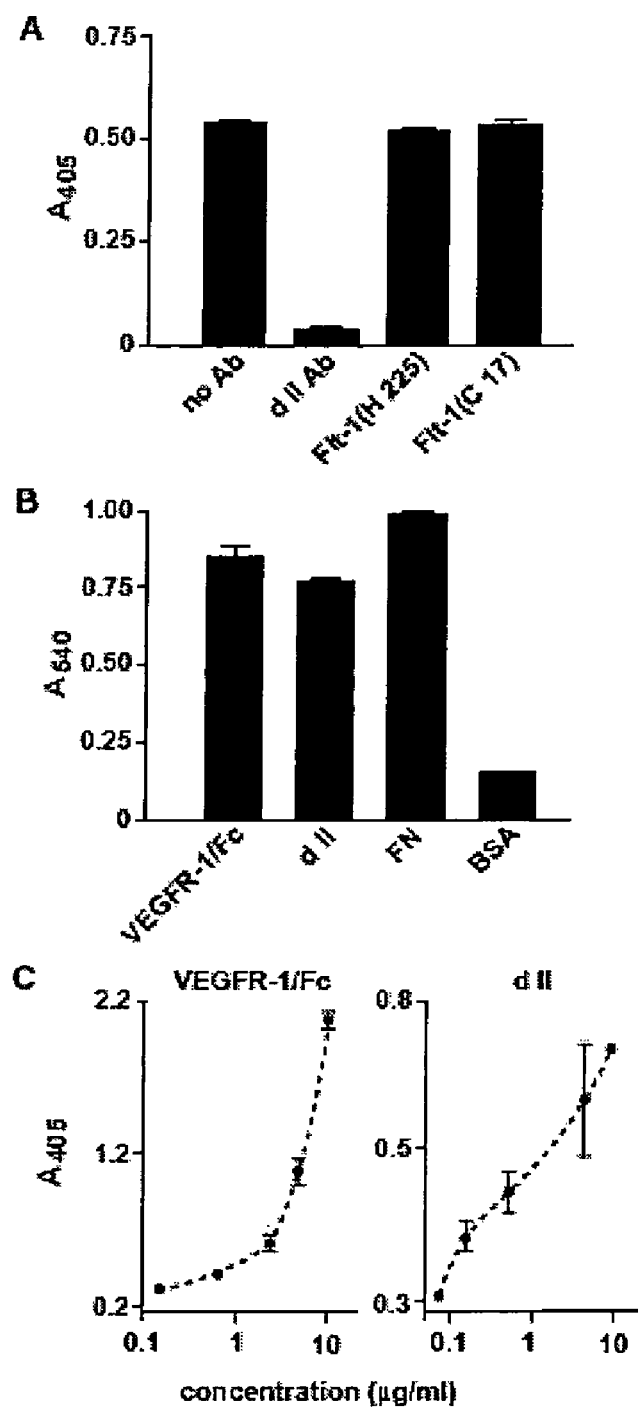
FIG. 1A shows the results of a solid-phase binding assay test of integrin α5β1 to sVEGFR-1 in the presence/absence of antibodies directed against specific regions of the sVEGFR-1 protein, the amount of bound protein was measure by colorimetric assay (absorbance at 405 nm).
FIG. 1B shows the results of a test of adhesion of the endothelial cells (EC) incubated on plates covered with sVEGFR-1, a protein fusion with the FC domain of human immunoglobulins (VEGFR-1 Fc), with the domain II type-Ig recombinant (d II), with fibronectin (FN) or bovine serum albumin (BSA), followed by colorimetric assay (absorbance at 540 nm).

The FIG. 1C shows the results of an adhesion test on solid phase of integrin α5β1 on plates covered with the domain II type-Ig recombinant or with VEGFR-1 Fc, followed by colorimetric assay (absorbance at 405 nm).

Figure 2:
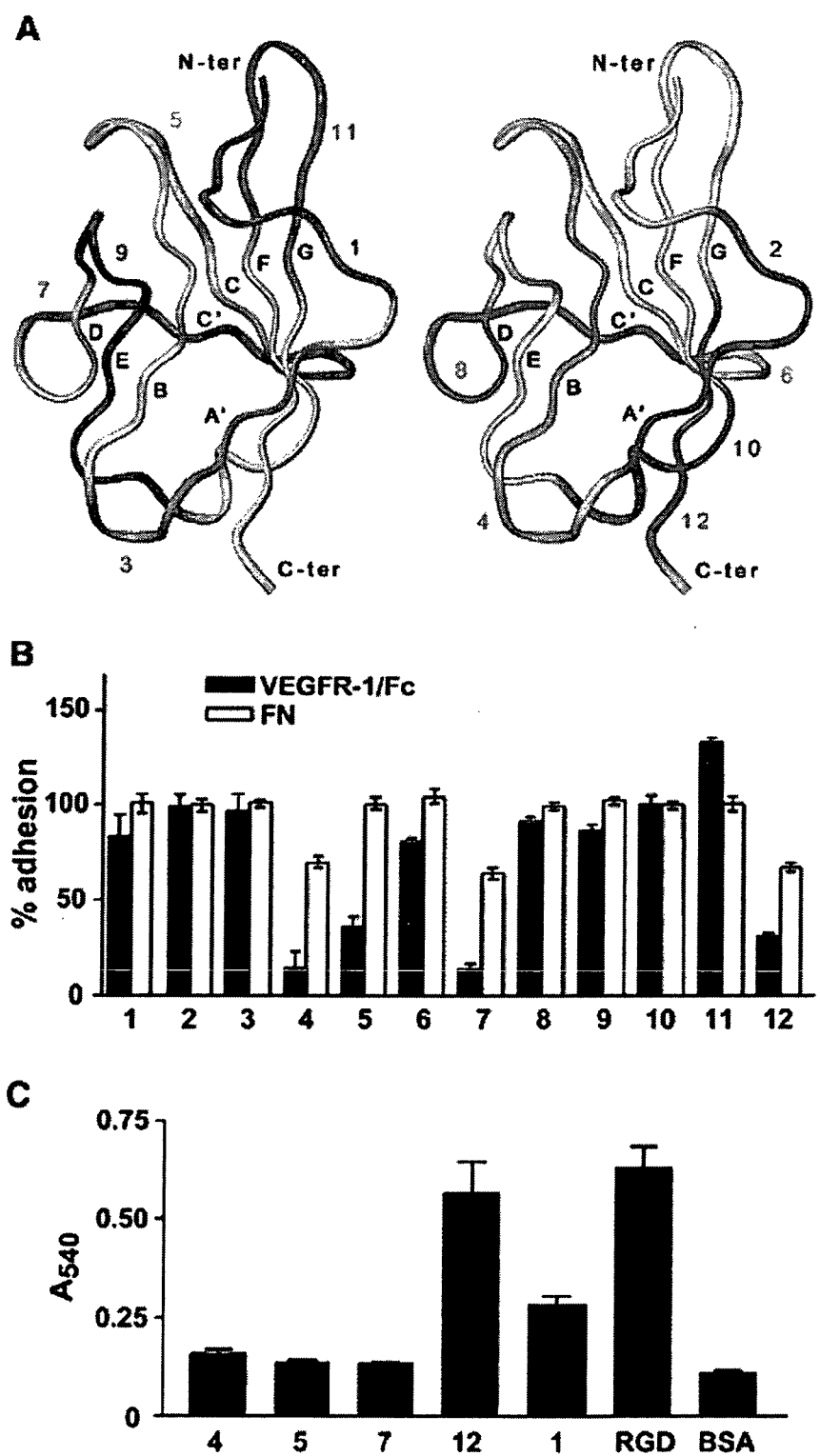

FIG. 2A shows in the right panel the location of peptides 2, 4, 5, 7, and 12 in the structure of domain II and in the left panel the location of peptides 1, 3, 5, 7, 9 and 11.

The FIG. 2B shows the results of a test of adhesion of the EC on plates covered with VEGFR-1/Fc or fibronectin, in the presence of the twelve peptides, the result is expressed as percentage of EC adhesion on the same substrates in the absence of peptides.

The FIG. 2C shows the results of a test of adhesion of EC on plates covered with peptides 4, 5, 7, 12, 1 and RGD, followed by calorimetric assay (absorbance at 540 nm).

Figure 3:
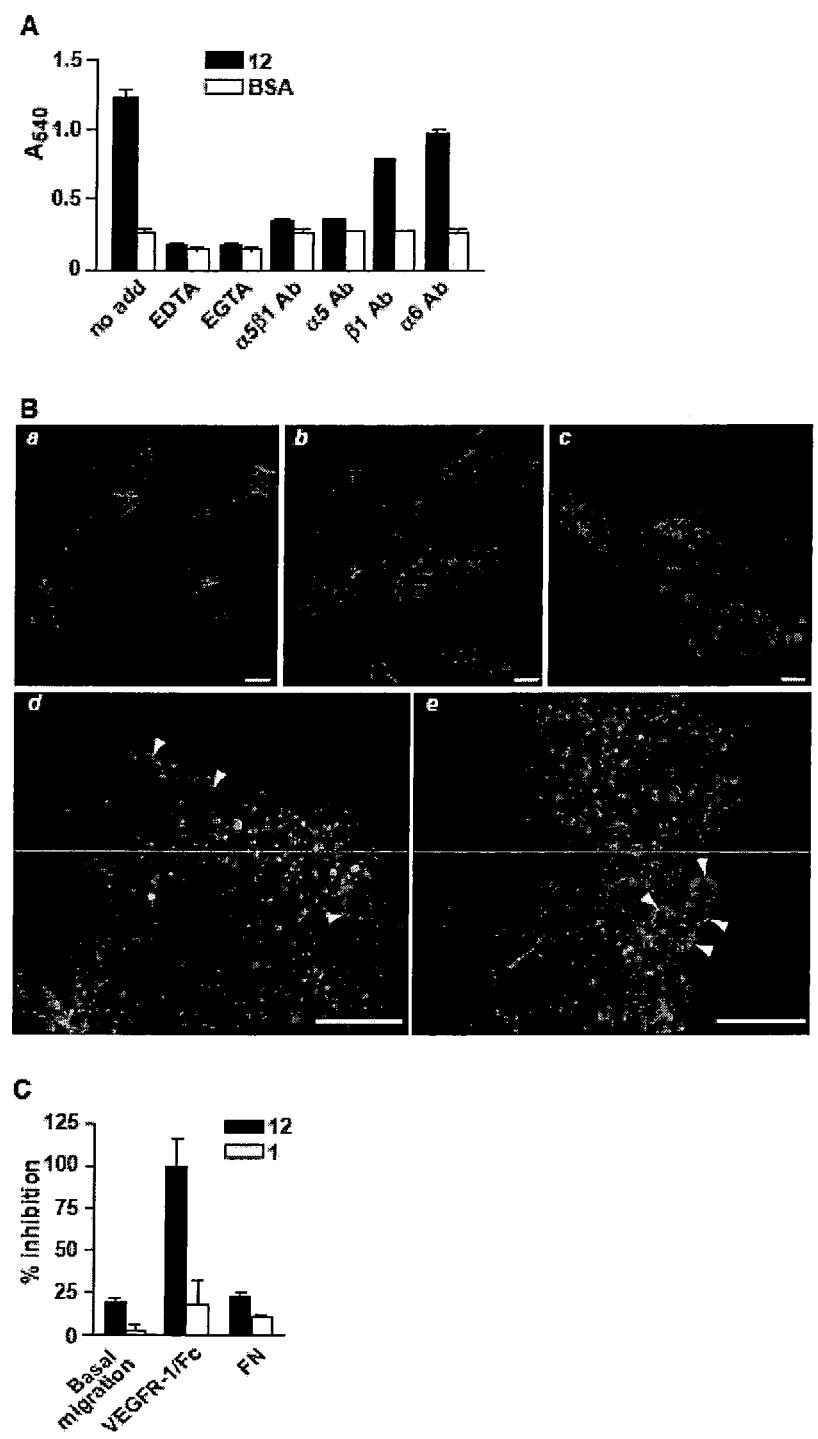

FIG. 3A shows the results of a test of adhesion of the EC on plates covered with peptide 12 in the presence of EDTA, EGTA, an antibody against $\alpha5\beta1$, $\alpha5$, $\beta1$ and $\alpha6$, followed by calorimetric assay (absorbance at 540 nm).

The FIG. 3B shows, in panels a-e, the results of an immunostaining for integrin $\alpha5\beta1$ of the EC incubated with magnetic beads coated with RGE peptide (panel a), RGD peptide (panel b, d) or with peptide 12 (panel c, e)

FIG. 3C shows the results of a test of migration of EC induced by VEGF-1/Fc or fibronectin (FN) in the presence of the peptide 1 or 12, the result is expressed as percentage of inhibition of migration observed in the absence of peptides.

Figure 4:
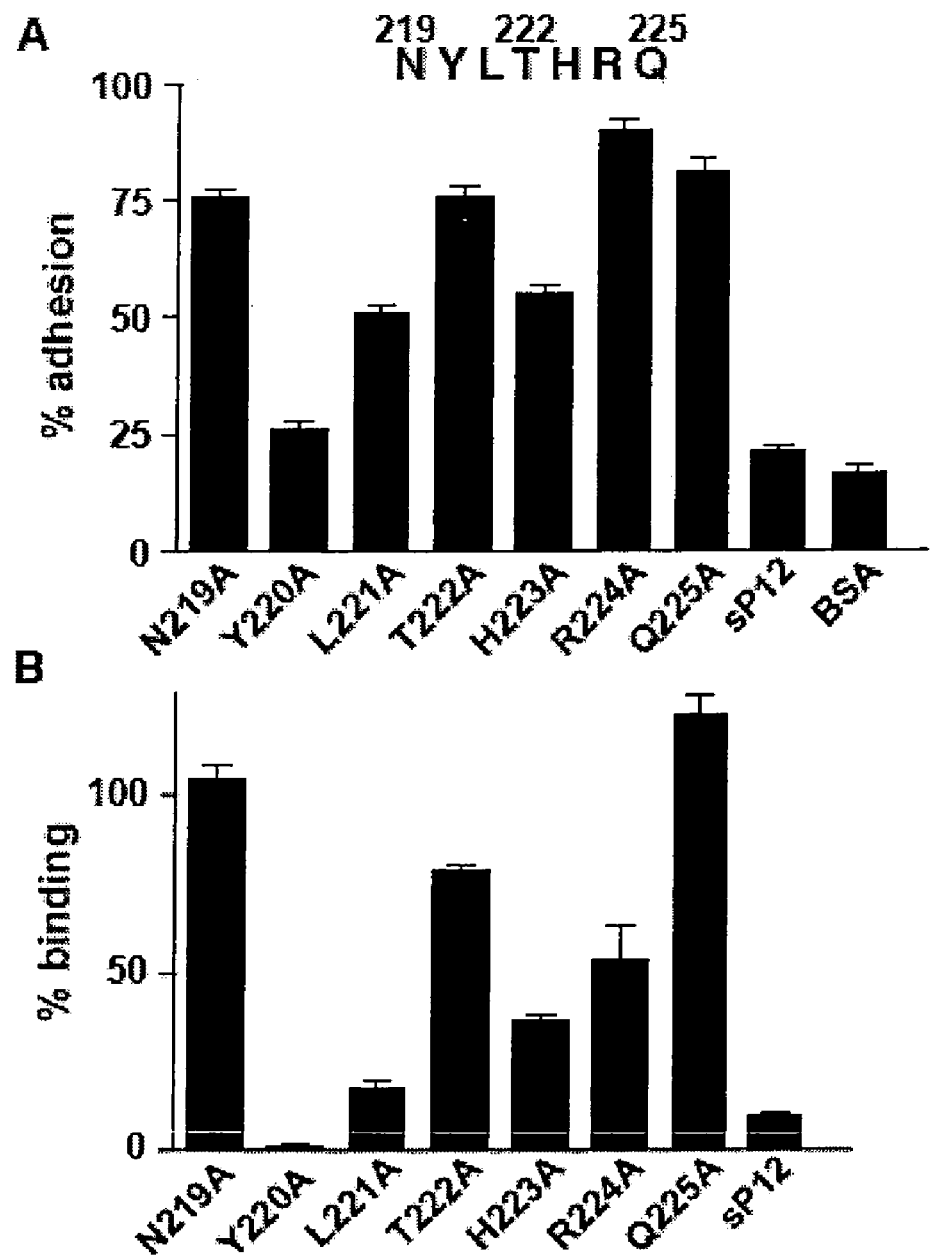

The FIG. 4A shows the effect of the replacement with alanine of various aminoacidic residues in peptide 12 on the cellular adhesion.

The FIG. 4B shows the effect of the replacement with alanine of different aminoacidic residues in the peptide 12 in binding the integrin $\alpha5\beta1$.

Figure 5:
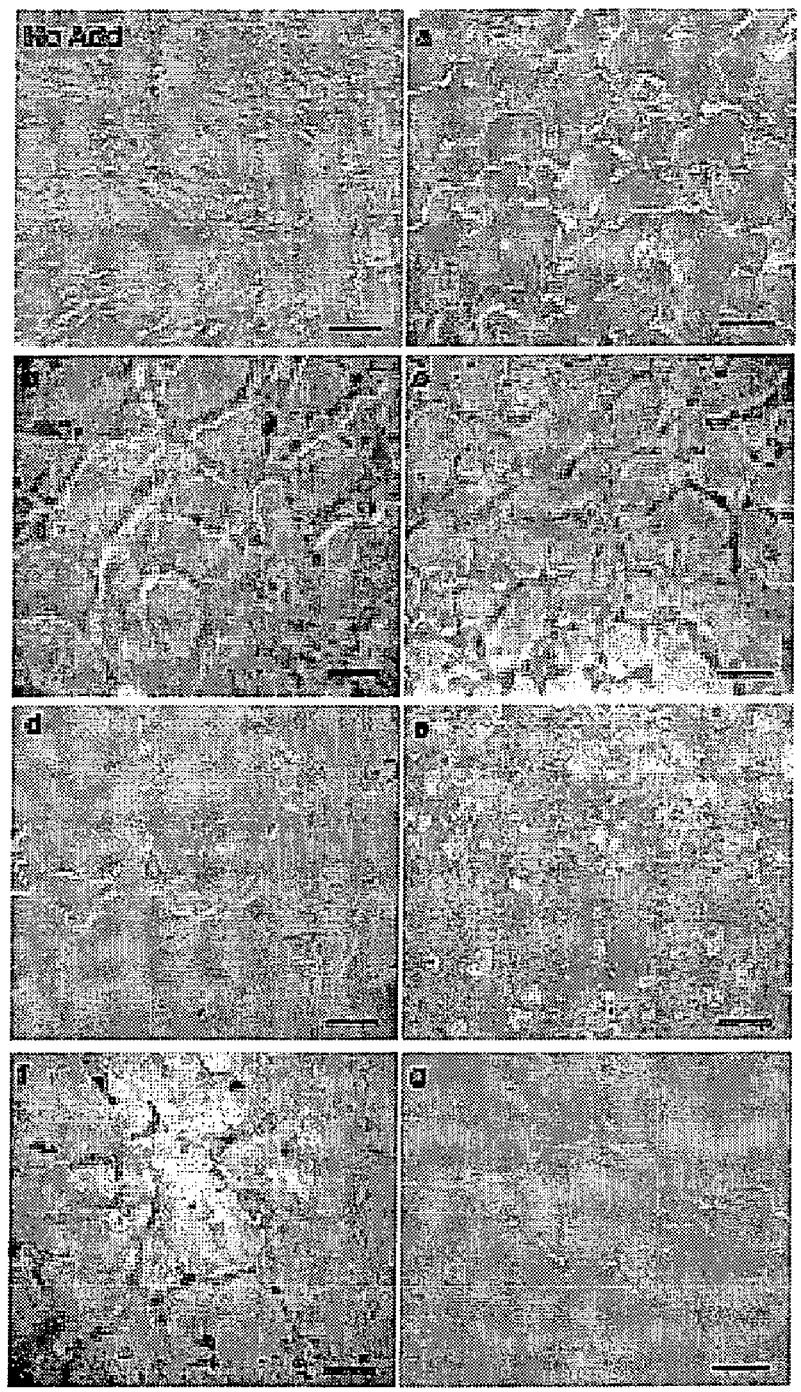

FIG. 5 shows the results of a test of endothelial vessel formation in the presence or absence of peptide 12 (panels a g), Q225A (panel c), Y220A (panel d), and concentrations of VEGF (100 nM) (panels b, d), and 20 mg/ml VEGFR-1 Fc (panels e, f, g).

Figure 6:
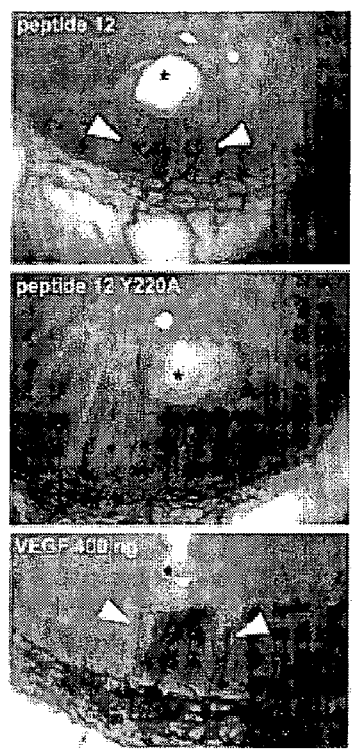
Figure 6:
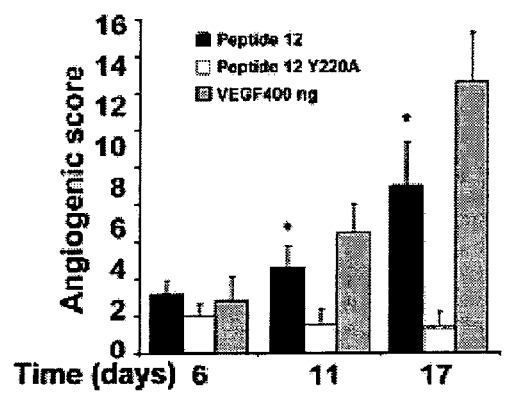
Figure 6:
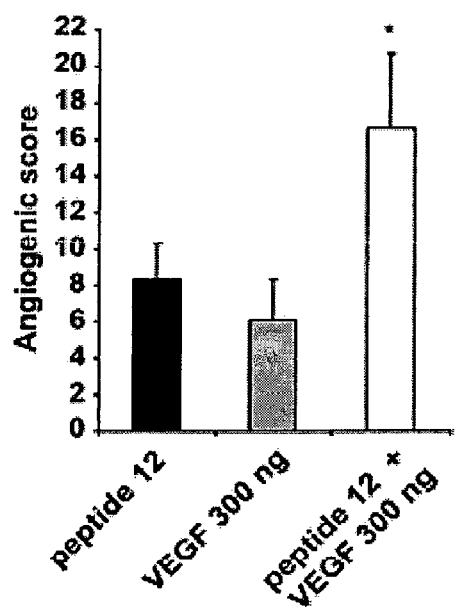

The FIGS. 6A and 6B show the effect on angiogenesis of the peptide 12 or Y220 compare to VEGF at different concentrations.

Figure 7:
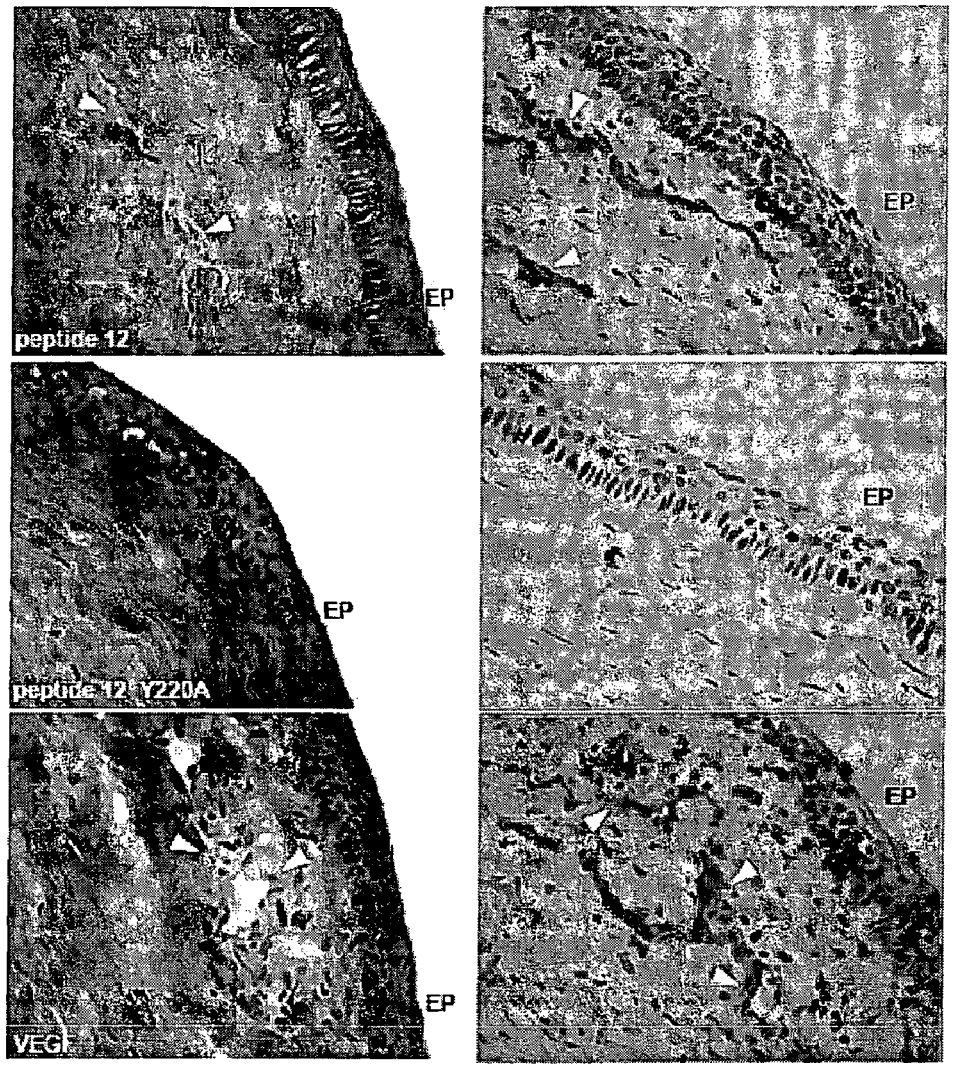

FIG. 7 shows the results of histological and immunohistochemical analysis of corneal angiogenesis.

1. Effect of the Antibody to Recognize a Peptide Whose Sequence is Present in VEGFR-1 Domain II on the Interaction sVEGFR-1/Integrin It is known that the integrin $\alpha5\beta1$ bind the VEGFR-1/Fc protein; and having previously demonstrated, the same inventors, than an antibody, able to recognize a peptide whose sequence is present in VEGFR-1 domain II, competes with the adhesion of the EC to the sVEGFR-1 mediated from the integrin $\alpha5\beta1$; the effect of the same antibody was analyzed (able to recognize a peptide whose sequence is present in VEGFR-1 domain II) on the direct interaction sVEGFR-1/integrin.

In a binding test on solid phase, dishes covered with VEGFR-1/Fc were dealt with various antibodies anti-VEGFR-1 and incubated with the purified integrin $\alpha5\beta1$, the amount of integrin bind was quantified by means of incubation with an antibody anti-integrin $\alpha5\beta1$ and colorimetric identification of this last one. The capacity of the antibody to recognize a peptide whose sequence is present in domain II of VEGFR-1 (dII Ab) completely inhibited the binding of the integrin $\alpha5\beta1$ with the VEGFR-1. A polyclonal antibody (Flt-1 H225) directed against a proteic fragment comprising the aminoacidic residual from 1 to 225 of the VEGFR-1, did not inhibit the VEGFR-1/integrin interaction. As expected the inhibition was not obtained with an antibody (Flt-1 C17) directed against the intracellular domain of VEGFR-1 (FIG. 1A).

2. Construction of a Recombinant Protein Correspondent to VEGFR-1 Domain Ii

Based on the domain boundaries observed in the experimentally determined structures available from the PDB database (www.rcsb.org), was designed a recombinant protein corresponding to domain II (residues 129-229). The protein was produced in cell line insect SF9 using the system of expression mediated by baculovirus and purified by affinity chromatography. The recombinant protein had the molecular weight expected on SDS-PAGE and was recognized by a polyclonal antibody anti-VEGFR-1.

The full cDNA of VEGFR-1 used for the production of the domain II recombinant was kindly provided by Dr. Shibuya (Institute of medical science, University of Tokyo, Japan). The cDNA was modified in the laboratory of Dr. Ballmer-Hofer (Paul-Scherrer Institut, Villigen-PSI, Switzerland) to introduce the site KPN I followed by a Kozak sequence, a start codon to the 5' end, a site BSI WI followed by an HA tags and a stop codon at the 3' end. The polylinker of the vector pFast-Bac 1 of Baculovirus (Invitrogen-Life Technologies) was replaced with a linker containing a site KPN I and a BSI WI together with a His tag.

Firstly, the full cDNA of VEGF-1 was cloned in pFastBac 1 using the sites KPN I and the BSI WI. To build the domain II Recombinant, the signal sequence of VEGFR-1 was amplified by PCR using the oligonucleotides:

```
                                            (SEQ ID NO: 1)
5'-GCGCGGATCCGGTACCGC-3'
and (SEQ ID NO: 2)
5'-GTGATGCGTACGTGAACCTGAACTAGATCCTGTG-3'
``` and cloned into. PFastBac previously modified.

Then the domain II was amplified with the oligonucleotides:

```
                                            (SEQ ID NO: 3)
5'-GTGATGCGTACGAGTGATACAGGTAGACCTTTC-3'
and (SEQ ID NO: 4)
5'-GTGATGCGTACGTCCGATTGTATTGGTTTGTCGATG-3'.
```

The PCR fragment was cloned into the modified pFastBac vector carrying the VEGFR-1 signal sequence. Recombinant Baculovirus was obtained using the Bac-to-Bac system (Invitrogen-Life Technologies). SF9 (Spodoptera frugiperda) cell line was purchased from Invitrogen, and maintained in culture at 27° C. in TC100 medium (Invitrogen-Life Technologies) containing 10% heat inactivated fetal calf serum. Infected SF9 cells were cultured in serum free SF-900 medium (Invitrogen-Life Technologies). For protein expression, SF9 cells were grown up to 60% confluence and infected with recombinant virus. Forty-eight hours post-infection cells were collected, and the recombinant protein was purified by affinity chromatography using the B-PER His Fusion Protein purification kit (PIERCE, Rockford, Ill.).

3. Ability of Domain II to Support the Adhesion of the EC

The endothelial cells derived from human umbilical vein (HUVEC) were used to examine ability of the domain II to support the adhesion of EC in plates covered with the recombinant protein.

The HUVEC were incubated on plates covered with VEGFR-1 FC, with the domain II (dII) recombinant, with fibronectin (FN) or bovine serum albumin (BSA). The protein VEGFR-1/Fc, and the fibronectin were used as positive controls and BSA as negative control.

The cells assayed were coloured and the absorbance was measured.

The dII recombinant supported the adhesion of the HUVEC (FIG. 1B) in analogous way to the VEGFR-1/Fc.

The direct bind of the integrin α5β1 to the domain had been determined also with binding test on solid phase. The purified integrin α5β1 was added to plates covered with dII or with VEGFR-1/Fc like positive control and the integrin bound was measured using an antibody anti-integrin α5β1 and a colorimetric test. As shown in FIG. 1C a similar amount of integrin interacted with the VEGFR-1/Fc and the dII recombinant.

4. Chosen of Peptides on VEGFR-1 Domain II

In order to identify a region of domain II potentially interacting with the integrin α5β1, were employed the determined structures of the domain with X-ray crystallography available in the data bank PDB. The three-dimensional structures were examined in order to identify the contiguous aminoacidic sequences on the surface of the protein that could mimic all the exposed region of domain II.

Twelve peptides (table I), were elaborate based on the following criteria:

1) they are on the protein surface and have high overall solvent accessible surface area;
2) they correspond to different regions of the domain surface, covering it almost entirely;
3) they are shorter than 15 residues;
4) they contain an high percentage of polar residues and, whenever possible, residues charged at physiological pH values (Asp, Glu, Lys and Arg);
5) they contain a low percentage of hydrophobic residues (i.e. Leu, Val, Ile, Met, Phe and Trp), to minimize solubility problems;
6) they do not contain Cys residues, which might lead to formation of dimeric peptides.

TABLE I

| P1 | GRPFVEMYSE | 132-141 | SEQ ID NO: 5 |
|---|---|---|---|
| P2 | YSEIPEIIH | 139-147 | SEQ ID NO: 6 |
| P3 | ETTHMTEGR | 144-152 | SEQ ID NO: 7 |
| P4 | TEGRELVIPARVT | 149-161 | SEQ ID NO: 8 |
| P5 | NITVTLKKFPL | 164-174 | SEQ ID NO: 9 |
| P6 | KKFPLD | 170-175 | SEQ ID NO: 10 |
| P7 | KFPLDTLIPDG | 171-181 | SEQ ID NO: 11 |
| P8 | DTLIPDGKRII | 175-185 | SEQ ID NO: 12 |
| P9 | DSRKGFIISNAT | 107-198 | SEQ ID NO: 13 |
| P10 | TYIKEIGL | 198-204 | SEQ ID NO: 14 |
| P11 | EATVNGHLYKT | 208-218 | SEQ ID NO: 15 |
| P12 | NYLTHRQ | 219-225 | SEQ ID NO: 16 |
| sP12 | LTQNYRH | — | SEQ ID NO: 17 |

To satisfy the requirement 6, VEGFR-1 residue Cys 158 was replaced by Ala in peptide 4. Additionally, to explore whether the presence of two branched hydrophobic residues next to each other might cause solubility problems, the adjacent Ile 145 and Ile 146 were both replaced by Thr in peptide 3. The sequence of peptide 5 has been previously published and reported to act as an angiogenesis inhibitor without binding to VEGF or inhibiting VEGF binding to its receptors.

5. Test on the Ability to Twelve Peptides to Inhibit the Adhesion Mediated from α5β1 of the EC to VEGFR-1

In order to test the ability of the twelve chosen peptides to inhibit the adhesion of the EC to VEGFR-1 mediated from the integrin α5β1, every peptide was added to one suspension of HUVEC before plated on dishes covered with VEGFR-1/Fc or fibronectin (FN). The data were indicated as percentage of adhesion, calculated to the number of cells adhered on the substrate itself in absence of peptides.

Like shown in FIG. 2B peptides 4, 5, 7, and 12 effectively blocked the adhesion of the EC to VEGFR-1/Fc. Moreover, peptides 4, 7 and 12 were able to partially inhibit the adhesion of the EC to the fibronectin, being suggested some interference with the binding site of the integrin α5β1.

Localization of peptides 4, 7 and 12 on the structure of VEGFR-1 domain II is shown in FIG. 2A ribbon representation of the track of carbon determined by x-ray crystallography): peptide 4 nearly overlaps entire to the chain B inside of the first (ABED) beta sheet; peptide 12 is localized on the opposite beta sheet inside of the chain G to the C terminal of the domain; peptide 7 comprises part of chain C, chain C', and loop C' D, that connects the two beta sheets one to the other.

6. Effects of Peptides on the Adhesion of the EC

To establish whether the four peptides, were able to inhibit the adhesion of the EC to VEGFR-1, by supporting directly the adhesion of the EC, the peptides were linked covalently to plates and the HUVEC were incubated on plates for 1 hour. The peptide 1 was used as negative control and the peptide RGD as the positive control. Unspecific adhesion was measured by absorbance in the plates covered with BSA. In this test only peptide 12 induced the adhesion of EC (FIG. 2C).

7. Interference of the Divalent Cations on the Adhesion of the EC to Peptide 12

The binding of proteins of the extracellular matrix to the integrins is generally dependent on the presence of the divalent cations, then it was investigated the interference of divalent cations with the adhesion of the EC to peptide 12. The peptide 12 or the BSA, as non-specific adhesion control, were linked on plates and the HUVEC added in the presence of chelating agents (EDTA or EGTA).

As shown in FIG. 3A treatment with EDTA OR EGTA completely abolished adhesion of EC indicating that the adhesion of the EC to peptide 12 requires divalent cations.

In order to demonstrate that the integrin α5β1 was the protein that mediated the adhesion of the EC to peptide 12, anti-integrin antibody was tested. The HUVEC were pre-incubated with an antibody against the integrin α5β1 or versus the integrinic subunit α6 and left to adhere on plates covered with peptide 12 or BSA. The pre-incubation of the HUVEC with the antibody against the integrin α5β1 inhibited the adhesion of the EC to peptide 12, while the antibody against α6 was ineffective (FIG. 3A).

8. Induction of Integrin α5β1 Aggregation Upon Binding to Peptide 12

The integrins not linked are widely distributed on cellular membrane, but after the ligand binding and the activation merged in distinct structures called focal contacts and ECM contact.

It was examined whether the peptide 12 was able to induce aggregation of integrin α5β1 after the binding. EC adherent cells were incubated with magnetic beads coated with peptide 12, or peptide RGD or peptide RGE respectively as positive and negative controls, and immunostained with an antibody against integrin α5β1.

A separate colouring for integrin α5β1 was observed around the beads covered with the peptide 12 (FIG. 3B, panels c, e) similar to that observed for the beads covered with the peptide RGD (FIG. 3B, panels b, d). No beads covered with the peptide RGE was attached with HUVEC in this test (FIG. 3B, panel a).

9. Effects of Peptide 12 on Migration and Cellular Proliferation

In order to investigate the ability to peptide 12 to influence the migration of the EC induced from VEGFR-1/Fc, a process mediated from the integrin α5β1, the HUVEC were pre-incubated with peptide 12 and peptide 1 and placed in Boyden chambers in order to analyze the migration induced from VEGFR-1/Fc or fibronectin (FN). Data represent the average of 14 microscopic fields and are referred to as percentage of inhibition compared to the migration observed in the absence of peptides. As shown in FIG. 3C the peptide 12 completely annulled the migratory response induced by VEGFR-1 Fc while the incubation of cells with a control peptide was completely ineffective. The inhibitory effect of the peptide 12 on cell migration was specific to the VEGFR-1, while no significant inhibition was observed on migration induced by fibronectin.

10. Effects of Peptide 12 on The Formation of Vascular Structures

It was tested the ability of the peptide 12 to induce the formation of tubules of EC. HUVEC cells were plated on 24 wells plates previously covered with a mixture of gel Type I collagen, in the absence or presence of 500 µg/ml peptide 12 or peptide 1. A second layer of gel Type I collagen was placed on the adherent cells. As shown, in the absence or presence of peptides, were added, in the culture medium, different concentrations of VEGF (40 or 100 nM), or 20 µg/ml of protein VEGFR-1/Fc. The capacity of the peptide 12 to induce the formation of tubules in EC on the collagen I matrix was found similar to that of VEGF (FIG. 5). Furthermore, when the VEGF was used to low concentration (40 nM) the simultaneous treatment with the peptide 12 increased the formation of induced VEGF tubules. On the contrary, the peptide 1 did not induce the formation of tubules neither increased the effect of VEGF. The addition of VEGFR-1 Fc, that negatively regulate the function of VEGF through the sequestration of growth factor and the consequent inhibition of its interaction with the tyrosine kinase isoform of the receptor, was used as negative control and led to a strong inhibition of the constitution of tubules.

To address the angiogenic role, in vivo, pellets releasing peptide 12 were implanted into rabbit corneal tissue and neovascularization was monitored for 17 days. As shown in FIG. 6A and FIG. 7 peptide 12 strongly promoted neoangiogenesis.

In presence of VEGFR-1/Fc, peptide 12 partially maintained its ability to induce the formation of vascular structures suggesting that its mechanism of action is independent from that of VEGF (data not shown).

11. Identification of the Residues of the Peptide 12 Involved in the Binding with Integrin To determine which residues of the peptide 12 had a role in the adhesion with integrin α5β1, were synthesized ten different peptides, each having a single or double replacement with alanine (ALA). These peptides were tested for their ability to directly support the cellular adhesion. The ten peptides were covalently linked to plates, and were also tested, as negative controls, a peptide "scrambled" in which the amino acid sequence of the peptide 12 was modified (see Table 1.) (sP12) and BSA. The HUVEC were plated and allow to adhere. The results were expressed as percentage of the cellular adhesion observed on plates covered with the peptide 12.

As shown in FIG. 4A, the replacement of only 3 residues with ALA influence the capacity of the peptide 12 to support the adhesion of EC: the replacement of Tyr 220 with ALA completely abolished cellular adhesion to peptide, the mutation of Leu 221 in ALA resulted in a partial reduction in the cellular adhesion, comparable to that observed in His 223 peptide mutant in Ala. These results demonstrated that the residues which are important in mediate the binding of the cells are Tyr 220 Leu 221 and His 223. Was also assessed the direct binding to integrin α5β1 with mutant peptides by a binding test on solid phase. The integrin α5β1 purified was added to plates covered with the various peptides and the amount bound was measured using an antibody anti-integrin α5β1 with a calorimetric method. The data were expressed as percentage of protein linked observed on plates covered with the original peptide 12.

As shown in FIG. 4B, the Tyr 220 is the residue more critical to the integrin binding and Leu 221 that His 223 are important in supporting the protein/protein interaction. Differently from cellular adhesion, Arg 224 also plays a role in mediating the binding of integrin with the peptide 12.

The peptide 12 is located at the C terminus of the G chain of Domain II (FIG. 2A). Its residues are accessible to solvent, with the exception of Tyr 222 whose side chain was close in the central core of the domain. The side chain of Tyr 220 is partially protected from the solvent by the carboxylate group of the Glu 144 in the side chain. The last residue is, however, highly flexible, as demonstrated by the high values of B factor in all crystalline structures of domains available, and from the conformational variability observed in the NMR structures.

Therefore, it is assumed that Tyr 220 was available for the binding with the ligand.

12. Specificity of the Residues YLXHR

In order to verify the specificity of residual YLXHR (X=whichever residual one) in extracellular proteins, the annotated human proteins from the UniProtKB/Swissprot consortium had been searched for its recurrence. The motif was found in 20 (0.2%) of 8,687 analyzed proteins, nobody of which was extracellular, suggesting that this sequence of binding for the integrin α5β1 is peculiar of the sVEGFR-1.

On the contrary, the motif RGD was found again in 7.9% of all human proteins and was more frequent in extracellular proteins (9.7%).

As stated in the experiments described detail here, the research have led to many important results, the following are summarised:

- the two isoforms, derived from alternative splicing of the VEGF receptor-1 play a different biological role during angiogenesis. In particular, the transmembrane isoform of the receptor is a tyrosine kinase, while the soluble form acts as molecule in extracellular matrix, involved in adhesion and cell migration, that as negative regulator of the activity of VEGF signal.
- an antibody against a peptide whose sequence is present in the domain II of VEGFR-1 inhibits cellular adhesion on areas covered with sVEGFR-1 and blocks the interaction with integrin $\alpha 5\beta 1$.
- a fragment of VEGFR-1, corresponding to the domain II, directly bind integrin $\alpha 5\beta 1$ and is sufficient to support the adhesion of the endothelial cells (EC).
- of the twelve peptides, that mimic selected regions of the surface of the receptor, four peptides (4, 5, 7 and 12) inhibit cellular adhesion to sVEGFR-1.
- the peptide 12 is the only that directly supports the adhesion of EC, and therefore interacts directly with integrin $\alpha 5\beta 1$. In fact, the binding EC/peptide 12 is sensitive to divalent cations and is inhibited by antibodies against integrin $\alpha 5\beta 1$.
- the direct interaction between the peptide 12 and integrin activate integrin.
- Peptide 12 inhibits the induced cellular migration from VEGFR-1, process that is mediated by the integrin $\alpha 5\beta 1$.
- Peptide 12 is able to induce in vitro the formation of vascular structures (tubules), suggesting that sVEGFR-1, the whose domain II contains sequence of peptide 12 is involved in the formation of blood vessels, adhesion and migration of the endothelial cells and is a positive modulator of blood vessels morphogenesis.
- three residues of the peptide 12, Tyr 220, Leu 221 and His 223 if mutated, significantly reduce the capacity of the peptide support cellular adhesion.
- the motif having sequence YLXHR, represents the region, in the domain II of the receptor VEGFR-1, strictly necessary for the interaction with integrin.
- This sequence does not interact with growth factors, VEGF and PLGF, therefore, although the residue responsible for the binding with the growth factors and integrin are close, the two interactions may be mutually exclusive.

Finally the biological effects of VEGF-1 on the endothelial cells and the identification of molecules interfering the different functions of this receptor could be the basis for the development of more effective therapeutic products.

In fact, the gene sequence YLXHR could be effectively used as a proangiogenic agent, in the treatment of clinical conditions that require triggering of cell angiogenesis.

These clinical conditions are included in group consisting of:

Hypertension, peripheral vascular pathologies diabetes-dependent, wounded, ischaemia of: muscle, brain, kidney, gut, heart or the arts; vascular pathologies occlusive or obstructive serious, peripherals vascular pathologies, pericardial ischaemia, myocardial infarction, diseases of the coronary arteries, cerebral vascular pathologies, visceral vascular pathologies.

REFERENCES

Berman, H. M., Westbrook, J., Feng, Z., Gilliland, G., Bhat, T. N., Weissig, H., Shindyalov, I. N. & Bourne, P. E. (2000) Nucleic Acids Res 28, 235-242.

Carmeliet, P., Moons, L., Luttun, A., Vincenti, V., Compernolle, V., De Mol, M., Wu, Y., Bono, F., Devy, L., Beck, H., Scholz, D., Acker, T. & DiPalma, T. (2001) Nat Med 7, 575-583.

Christinger, H. W., Fuh, G., de Vos, A. M. & Wiesmann, C. (2004) J Biol Chem 279, 10382-10388.

Davis-Smyth, T., Presta, L. G. & Ferrara, N. (1998) J Biol Chem 273, 3216-3222.

Dayringer, H. E., Tramontano, A., Spang, S. R. & Fletterick, R. J. (1986) J Mol Graph 4, 82-87.

Folkman, J. (1995) N Engl J Med 333, 1757-1763.

Fong, G., Rossant, J., Gertsenstein, M. & Breitman, M. (1995) Nature 376, 66-70.

Fong, G., Zhang, L., Bryce, D. & Peng, J. (1999) Development 126, 3015-3025.

Francis, S. E., Goh, K. L., Hodivala-Dilke, K., Bader, B. L., Stark, M., Davidson, D. & Hynes, R. O. (2002) Arterioscler Thromb Vasc Biol 22, 927-33.

Fuh, G., Garcia, K. C. & de Vos, A. M. (2000) J Biol Chem 275, 26690-26695.

Germani, A., Di Carlo, A., Mangoni, A., Straino, S., Giacinti, C., Turrini, P., Turrini, P., Biglioli, P. & Capogrossi, M. C. (2003) Am J Pathol 163, 1417-28.

Gimbrone, M. A. (1976) Prog Hemost Thromb 3, 1-28.

Hiratsuka, S., Minowa, O., Kuno, J., Noda, T. & Shibuya, M. (1998) Proc Natl Acad Sci USA 95, 9349-9354.

Humpries, M. J. (2000) Biochem Soc Trans 28, 311-229.

Inoue, T., Kibata, K., Suzuki, M., Nakamura, S., Motoda, R. & Orita, K. (2000) FEBS Lett 469, 14-18.

Ishida, A., Murray, J., Saito, Y., Kanthou, C., Benzakour, O., Shibuya, M. & Wijelath, E. (2001) J Cell Physiol 188, 359-68.

Kearney, J. B., Kappas, N. C., Ellerstrom, C., DiPaola, F. W. & Bautch, V. L. (2004) Blood 103, 4527-4535.

Kendall, R. L. & Thomas, K. A. (1993) Proc Natl Acad Sci USA 90, 10705-10709.

Kim, S., Bell, K., Mausa, S. A. & Varner, J. A. (2000) Am J Pathol 156, 1345-1362.

Koivunen, E., Gay, D. A. & Ruoslahti, E. (1993) J Biol Chem 268, 20205-20210.

Koivunen, E., Wang, B. & Ruoslahti, E. (1994) J Cell Biol 124, 373-80.

Korpelainen, E. & Alitalo, K. (1998) Curr Opin Cell Biol 10, 159-164.

Leahy, D. J., Aukhil, I. & Erickson, H. P. (1996) Cell 84, 155-164.

Leu, S., Lam, S. & Lau, L. (2002) J Biol Chem 277, 46248-55.

Mould, A. P., Burrows, L. & Humphries, M. J. (1998) J Biol Chem 273, 25664-25672.

O'Donovan, C., Apweiler, R. & Bairoch, A. (2001) Trends Biotechnol 19, 178-181.

Orecchia, A., Lacal, P. M., Schietroma, C., Morea, V., Zambruno, G. & Fulla, C. M. (2003) J Cell Sci 116, 3479-3489.

Roberts, D. M., Kearney, J. B., Johnson, J. H., Rosenberg, M. P., Kumar, R. & Bautch, V. L. (2004) Am J Pathol 164, 1531-1535.

Sawano, A., Iwai, S., Sakurai, Y., Ito, M., Shiara, K., Nakahata, T. & Shibuya, M. (2001) Blood 97, 785-791.

Shibuya, M., Yamaguchi, S., Yamane, A., Ikeda, T., Tojo, A., Matsushime, H. & Sato, M. (1990) Oncogene 8, 519-527.

Shimaoka, M. & Springer, T. A. (2003) Nat Rev Drug Discov 2, 703-716.

Tan, D. C. W., Manjunatha Kini, R., Jois, S. D. S., Lim, D. K. F., Xin, L. & Ge, R. (2001) FEBS-Lett 494, 150-156.

Wang, H. & Keiser, J. (1998) Circ Res 83, 832-840.

Wiesmann, C., Fuh, G., Christinger, H. W., Eigenbrot, C., Wells, J. A. & de Vos, A. M. (1997) Cell 91, 695-704.

Yamada, K. M. & Geiger, B. (1997) Curr Opin Cell Biol 9, 76-85.

---

The invention claimed is:

1. An isolated peptide consisting of the amino acid sequence YLXHR as set forth in SEQ ID NO: 18—SEQ ID NO: 36 and having proangiogenic activity.

2. The peptide according to claim 1, wherein the amino acid sequence is YLTHR as set forth in SEQ ID NO: 33 and having proangiogenic activity.

3. A method of preparing a pharmaceutical composition, comprising combining the peptide of claim 1 with a pharmacologically acceptable carrier.

4. A pharmaceutical composition, comprising the peptide according to claim 1 and a pharmacologically acceptable carrier.

* * * * *

SEQUENCE LISTING

<160> NUMBER OF SEQ ID NOS: 37

<210> SEQ ID NO 1
<211> LENGTH: 18
<212> TYPE: DNA
<213> ORGANISM: Homo sapiens

<400> SEQUENCE: 1
gcgcggatcc ggtaccgc                                              18

<210> SEQ ID NO 2
<211> LENGTH: 34
<212> TYPE: DNA
<213> ORGANISM: Homo sapiens

<400> SEQUENCE: 2
gtgatgcgta cgtgaacctg aactagatcc tgtg                            34

<210> SEQ ID NO 3
<211> LENGTH: 33
<212> TYPE: DNA
<213> ORGANISM: Homo sapiens

<400> SEQUENCE: 3
gtgatgcgta cgagtgatac aggtagacct ttc                             33

<210> SEQ ID NO 4
<211> LENGTH: 36
<212> TYPE: DNA
<213> ORGANISM: Homo sapiens

<400> SEQUENCE: 4
gtgatgcgta cgtccgattg tattggtttg tcgatg                          36

<210> SEQ ID NO 5
<211> LENGTH: 10
<212> TYPE: PRT
<213> ORGANISM: Homo sapiens

<400> SEQUENCE: 5

Gly Arg Pro Phe Val Glu Met Tyr Ser Glu
1               5                   10

<210> SEQ ID NO 6
<211> LENGTH: 9
<212> TYPE: PRT
<213> ORGANISM: Homo sapiens

<400> SEQUENCE: 6

Tyr Ser Glu Ile Pro Glu Ile Ile His
1               5

<210> SEQ ID NO 7
<211> LENGTH: 9
<212> TYPE: PRT

```
<213> ORGANISM: Homo sapiens

<400> SEQUENCE: 7

Glu Thr Thr His Met Thr Glu Gly Arg
1               5

<210> SEQ ID NO 8
<211> LENGTH: 13
<212> TYPE: PRT
<213> ORGANISM: Homo sapiens

<400> SEQUENCE: 8

Thr Glu Gly Arg Glu Leu Val Ile Pro Ala Arg Val Thr
1               5                   10

<210> SEQ ID NO 9
<211> LENGTH: 11
<212> TYPE: PRT
<213> ORGANISM: Homo sapiens

<400> SEQUENCE: 9

Asn Ile Thr Val Thr Leu Lys Lys Phe Pro Leu
1               5                   10

<210> SEQ ID NO 10
<211> LENGTH: 6
<212> TYPE: PRT
<213> ORGANISM: Homo sapiens

<400> SEQUENCE: 10

Lys Lys Phe Pro Leu Asp
1               5

<210> SEQ ID NO 11
<211> LENGTH: 11
<212> TYPE: PRT
<213> ORGANISM: Homo sapiens

<400> SEQUENCE: 11

Lys Phe Pro Leu Asp Thr Leu Ile Pro Asp Gly
1               5                   10

<210> SEQ ID NO 12
<211> LENGTH: 11
<212> TYPE: PRT
<213> ORGANISM: Homo sapiens

<400> SEQUENCE: 12

Asp Thr Leu Ile Pro Asp Gly Lys Arg Ile Ile
1               5                   10

<210> SEQ ID NO 13
<211> LENGTH: 12
<212> TYPE: PRT
<213> ORGANISM: Homo sapiens

<400> SEQUENCE: 13

Asp Ser Arg Lys Gly Phe Ile Ile Ser Asn Ala Thr
1               5                   10

<210> SEQ ID NO 14
<211> LENGTH: 7
<212> TYPE: PRT
<213> ORGANISM: Homo sapiens

<400> SEQUENCE: 14
```

```
Thr Tyr Lys Glu Ile Gly Leu
1               5
```

<210> SEQ ID NO 15
<211> LENGTH: 11
<212> TYPE: PRT
<213> ORGANISM: Homo sapiens

<400> SEQUENCE: 15

```
Glu Ala Thr Val Asn Gly His Leu Tyr Lys Thr
1               5                   10
```

<210> SEQ ID NO 16
<211> LENGTH: 7
<212> TYPE: PRT
<213> ORGANISM: Homo sapiens

<400> SEQUENCE: 16

```
Asn Tyr Leu Thr His Arg Gln
1               5
```

<210> SEQ ID NO 17
<211> LENGTH: 7
<212> TYPE: PRT
<213> ORGANISM: Homo sapiens

<400> SEQUENCE: 17

```
Leu Thr Gln Asn Tyr Arg His
1               5
```

<210> SEQ ID NO 18
<211> LENGTH: 5
<212> TYPE: PRT
<213> ORGANISM: Homo sapiens

<400> SEQUENCE: 18

```
Tyr Leu Ala His Arg
1               5
```

<210> SEQ ID NO 19
<211> LENGTH: 5
<212> TYPE: PRT
<213> ORGANISM: Homo sapiens

<400> SEQUENCE: 19

```
Tyr Leu Arg His Arg
1               5
```

<210> SEQ ID NO 20
<211> LENGTH: 5
<212> TYPE: PRT
<213> ORGANISM: Homo sapiens

<400> SEQUENCE: 20

```
Tyr Leu Asn His Arg
1               5
```

<210> SEQ ID NO 21
<211> LENGTH: 5
<212> TYPE: PRT
<213> ORGANISM: Homo sapiens

<400> SEQUENCE: 21

```
Tyr Leu Asp His Arg
1               5
```

```
<210> SEQ ID NO 22
<211> LENGTH: 5
<212> TYPE: PRT
<213> ORGANISM: Homo sapiens

<400> SEQUENCE: 22

Tyr Leu Cys His Arg
1               5

<210> SEQ ID NO 23
<211> LENGTH: 5
<212> TYPE: PRT
<213> ORGANISM: Homo sapiens

<400> SEQUENCE: 23

Tyr Leu Glu His Arg
1               5

<210> SEQ ID NO 24
<211> LENGTH: 5
<212> TYPE: PRT
<213> ORGANISM: Homo sapiens

<400> SEQUENCE: 24

Tyr Leu Gln His Arg
1               5

<210> SEQ ID NO 25
<211> LENGTH: 5
<212> TYPE: PRT
<213> ORGANISM: Homo sapiens

<400> SEQUENCE: 25

Tyr Leu Gly His Arg
1               5

<210> SEQ ID NO 26
<211> LENGTH: 5
<212> TYPE: PRT
<213> ORGANISM: Homo sapiens

<400> SEQUENCE: 26

Tyr Leu Ile His Arg
1               5

<210> SEQ ID NO 27
<211> LENGTH: 5
<212> TYPE: PRT
<213> ORGANISM: Homo sapiens

<400> SEQUENCE: 27

Tyr Leu Leu His Arg
1               5

<210> SEQ ID NO 28
<211> LENGTH: 5
<212> TYPE: PRT
<213> ORGANISM: Homo sapiens

<400> SEQUENCE: 28

Tyr Leu Lys His Arg
1               5

<210> SEQ ID NO 29
```

```
<211> LENGTH: 5
<212> TYPE: PRT
<213> ORGANISM: Homo sapiens

<400> SEQUENCE: 29

Tyr Leu Met His Arg
1               5

<210> SEQ ID NO 30
<211> LENGTH: 5
<212> TYPE: PRT
<213> ORGANISM: Homo sapiens

<400> SEQUENCE: 30

Tyr Leu Phe His Arg
1               5

<210> SEQ ID NO 31
<211> LENGTH: 5
<212> TYPE: PRT
<213> ORGANISM: Homo sapiens

<400> SEQUENCE: 31

Tyr Leu Pro His Arg
1               5

<210> SEQ ID NO 32
<211> LENGTH: 5
<212> TYPE: PRT
<213> ORGANISM: Homo sapiens

<400> SEQUENCE: 32

Tyr Leu Ser His Arg
1               5

<210> SEQ ID NO 33
<211> LENGTH: 5
<212> TYPE: PRT
<213> ORGANISM: Homo sapiens

<400> SEQUENCE: 33

Tyr Leu Thr His Arg
1               5

<210> SEQ ID NO 34
<211> LENGTH: 5
<212> TYPE: PRT
<213> ORGANISM: Homo sapiens

<400> SEQUENCE: 34

Tyr Leu Trp His Arg
1               5

<210> SEQ ID NO 35
<211> LENGTH: 5
<212> TYPE: PRT
<213> ORGANISM: Homo sapiens

<400> SEQUENCE: 35

Tyr Leu Tyr His Arg
1               5

<210> SEQ ID NO 36
<211> LENGTH: 5
<212> TYPE: PRT
<213> ORGANISM: Homo sapiens
```

```
<400> SEQUENCE: 36

Tyr Leu Val His Arg
1               5

<210> SEQ ID NO 37
<211> LENGTH: 7
<212> TYPE: PRT
<213> ORGANISM: Homo sapiens

<400> SEQUENCE: 37

Asn Tyr Leu Thr His Arg Gln
1               5
```